United States Patent
Van Doorn et al.

(10) Patent No.: US 6,265,531 B1
(45) Date of Patent: *Jul. 24, 2001

(54) DIGLYCIDYLESTER OF ALKYLATED HEXAHYDROPHTHALIC ANHYDRIDE

(75) Inventors: Johannes Adrianus Van Doorn; Jozef Jacobus Titus Smits, both of Amsterdam (NL)

(73) Assignee: Shell Oil Company, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 56 days.

(21) Appl. No.: 09/082,256

(22) Filed: May 20, 1998

(30) Foreign Application Priority Data

May 22, 1997 (EP) .................................. 97201532

(51) Int. Cl.[7] .................................. C07D 301/30
(52) U.S. Cl. .................. 528/366; 525/423; 525/438; 525/510; 525/528; 525/533; 549/515
(58) Field of Search .................. 549/515; 528/366; 525/423, 438, 510, 528, 533

(56) References Cited

U.S. PATENT DOCUMENTS

| 3,629,295 | 12/1971 | Stackman et al. . |
| 3,644,431 | 2/1972 | Heer et al. . |
| 3,987,070 | * 10/1976 | Prater . |
| 4,562,274 | * 12/1985 | Rauleder et al. ............... 549/525 |
| 5,322,907 | 6/1994 | Cotting et al. ............... 525/438 |

FOREIGN PATENT DOCUMENTS

| 1245369 | 7/1967 | (DE) . |
| 2126280 | 12/1971 | (DE) . |
| 0506617 | 3/1992 | (EP) . |
| 0518408 | 12/1992 | (EP) . |
| 1360811 | 7/1974 | (GB) . |
| 1360812 | 7/1974 | (GB) . |
| 1360813 | 7/1974 | (GB) . |
| 55-133374 | 10/1980 | (JP) . |
| 62-218422 | 9/1987 | (JP) . |
| 01163211 | 6/1989 | (JP) . |

OTHER PUBLICATIONS

"Reaction Products of Alloocimene and Maleic Anhydride," by J. E. Milks and J. E. Lancaster, *Journal of Organic Chemistry*, vol. 30, 1965, pp. 888–891.

"Cis–Trans Isomerization of Alloocimene With Dienophiles and Other π–Acids," by E. K. von Gustorf and J. Leitich, *Tetrahedron Letters*, No. 45, 1968, pp. 4689–4692.

* cited by examiner

Primary Examiner—Robert E. L. Sellers

(57) ABSTRACT

A glycidylester of the general formula I

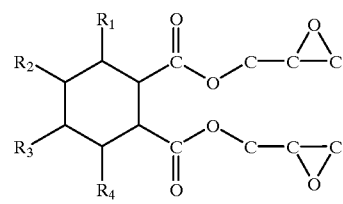

in which $R_1$ and $R_4$ are the same or different $C_1$–$C_6$ alkyl or $C_6$–$C_{10}$ cycloalkyl groups, and $R_2$ and $R_3$ are the same or different and are H or $C_1$–$C_6$ alkyl or $C_6$–$C_{10}$ cycloalkyl groups.

The glycidylester is used in a thermosetting resin composition, comprising also a curing compound and preferably an advanced resin product. The thermosetting resin composition can be applied for outdoor durable coatings, having excellent resistance against acid rain.

3 Claims, No Drawings

DIGLYCIDYLESTER OF ALKYLATED HEXAHYDROPHTHALIC ANHYDRIDE

The invention relates to a glycidylester and to a thermosetting resin composition comprising the glycidylester.

Resins based on α,α-branched dicarboxylic acids are known such as EP-A-0518408.

It has been demonstrated that coatings based on α,α-branched dicarboxylic acids (such as diethyl malonic acid) exhibit a good outdoor durability. Such α,α-branched dicarboxylic acids have been incorporated into binder resins via a sequence of reactions. Firstly, the acids were glycidated to form the corresponding diglycidylesters. Subsequently, a linear polyester was prepared via an advancement (i.e. fusion) reaction of an α,α-branched diacid with the corresponding diglycidylester. The hydroxyl groups of the resulting polyesters were used for the cross-linking reaction with a melamine resin.

However, according to the important paint manufacturers, the resistance towards acids (acidic rain) of these coatings is insufficient.

For this reason we have taken a new approach in the synthesis of an inexpensive feedstock for acid resistant coatings with acceptable UV resistance. We have found that α,β-substituted dicarboxylic acids are suitable base materials for outdoor durable coatings, having excellent resistance against acid rain.

Therefore the invention relates to a glycidylester of the general formula I

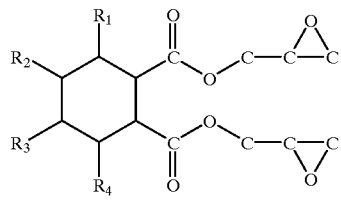

I in which $R_1$ and $R_4$ are the same or different $C_1$–$C_6$ alkyl or $C_6$–$C_{10}$ cycloalkyl groups, and $R_2$ and $R_3$ are the same or different and are H or $C_1$–$C_6$ alkyl or $C_6$–$C_{10}$ cycloalkyl groups.

Such structures can be prepared via a Diels-Alder reaction of maleic anhydride and a diene.

Allo-ocimene ((4E,6E)-2,6-dimethyl-2,4,6-octatriene) is a suitable starting compound. In this compound, the groups $R_1$ and $R_4$ (which are the β-substituents in the final product) are an isobutenyl- and a methyl group.

In fact, allo-ocimene is the best, thus preferred compound that comes in perspective for our objective.

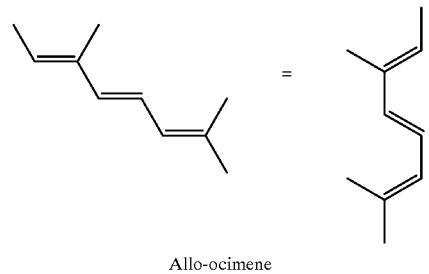

Allo-ocimene

The reaction of allo-ocimene and maleic anhydride gives compound (1). After hydrogenation, compound (2) is obtained that serves as a feedstock for acid resistant coatings.

The Diels-Alder reaction is in fact an addition reaction, it has a 100% atom utilisation, and produces no waste materials. The same is true for the hydrogenation and hydrolysis steps. There are, in theory two ways in which allo-ocimene and maleic anhydride can form a Diels-Alder adduct. This is because allo-ocimene has two butadiene fragments. Thus, two adducts are possible, compounds (1) and X. However, due to steric hindrance isomer X cannot form. Therefore, the reaction gives only one isomer (1); see Figure. I.

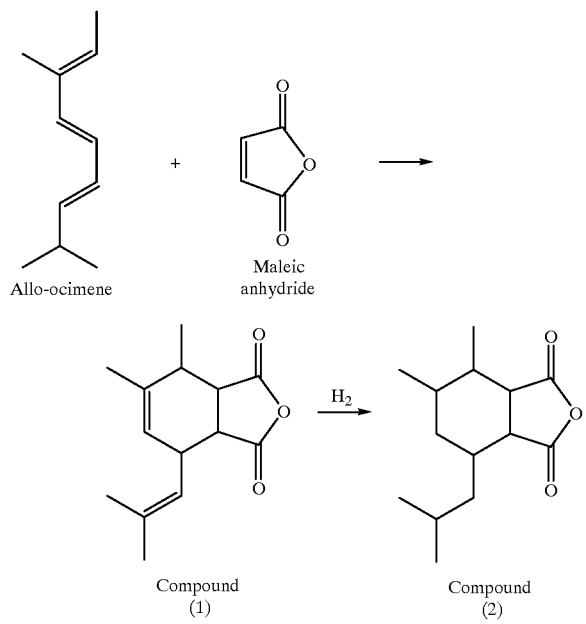

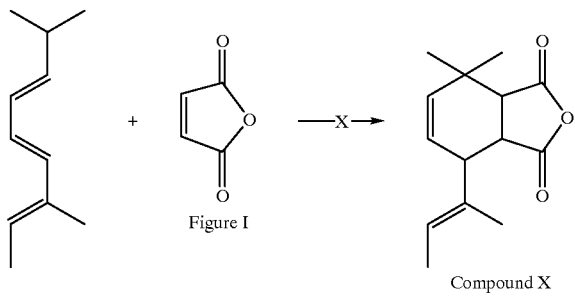

Figure I

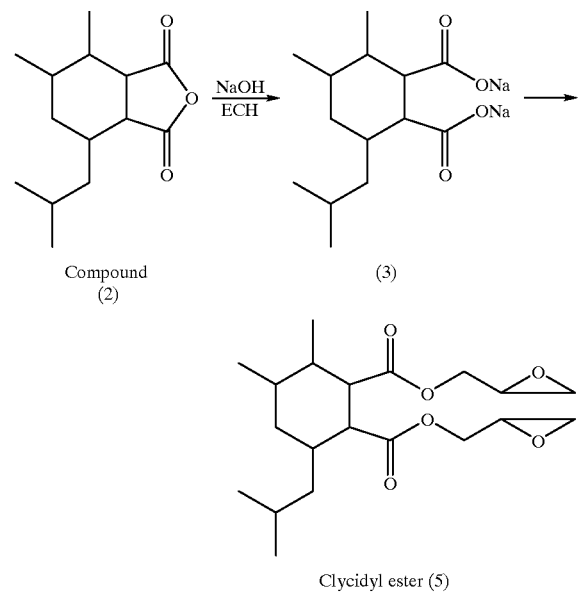

Compound X

The Diels-Alder reaction of allo-ocimene and maleic anhydride is reported in the literature.
See:
E. K. von Gustorf, J. Letich; Tetrahedron letters 45, 4689, (1968)
L. A. Goldblatt, S. Palkin; J. Am. Chem. Soc. 63, 3517, 3520 (1941)
Y. Chrétien-Bressiere; Annales de Chemie 13, 301, 331, (1957)
A. R. Vil'chinskaya, B. A. Arbuzov; J. Gen. Chem. USSR, 29, 2686, (1959)
J. E. Milks, J. E. Lancaster; J. Org. Chem., 30, 888, 890, (1965)
K. T. Joseph, G. S. Krishna Rao, Tetrahedron, 23, 519, (1967)
B. A. Arbuzov, Chemische Berichte 1968 (1934)

In these cases, the reagents are mixed without solvent or catalyst. Immediately after adding the solid maleic anhydride to the allo-ocimene, the liquid turns intensely orange. At room temperature no reaction takes place, since the maleic anhydride poorly dissolves in allo-ocimene. When the mixture is carefully heated to approximately 50° C., the reaction starts. The Diels-Alder reaction is very exothermic, the temperature reaches 170–190° C. within several minutes. During the course of the reaction, the orange/yellow color weakens. After 15 minutes the temperature starts to drop and after about 45 minutes the mixture solidifies as pale yellow crystals. The yield is almost quantitative. Adding the components in a different sequence (allo-ocimene to maleic anhydride) has no effect on the color, nor has purification of the allo-ocimene by distillation. We have found that the Diels-Alder reaction of allo-ocimene and maleic anhydride proceeds in very high yield (over 97%). Due to secondary orbital interactions in the transition state, we expected to form the isomer in which the methyl- and isobutenyl moiety are directed cis with respect to the anhydride moiety (compound 1). Literature data also predict this conformation.

The yellow anhydride (1) is hydrogenated, preferably in ethyl acetate using $PtO_2$ as a catalyst (Adams catalyst). The hydrogenation is advantageously carried out in an autoclave with magnetic stirring, using 30 bars of hydrogen. In approximately 2–3 hours, the consumption of hydrogen gas stops. The hydrogenated product, 2,3-dimethyl-5-isobutyl-hexahydrophthalic anhydride (2), is a slightly yellow colored, low-viscous oil.

The glycidation of the hydrogenated product (2) is preferably performed using per mole of anhydride an excess of 10 mole of epichlorohydrine (ECH). 9 Mole of isopropanol are added as co-solvent. The crude resin is advantageously submitted to a mild after dehydrochlorination treatment. This is suitably performed with a 30% solution of the resin in methylisobutylketon (MIBK) at 40° C. for 1 hour.

The yield of the glycidation reaction is extremely good, 97%. Some losses due to hydrolysis occur in the ADHC treatment, but the overall yield is still 87%.

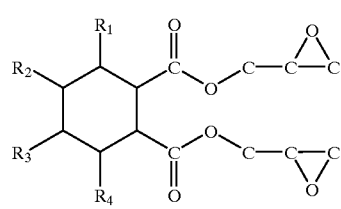

Compound (2) → (3)

Clycidyl ester (5)

The coatings based on this glycidylester show a combination of sufficient UV stability and high acid resistance.

The invention further relates to a thermosetting resin composition comprising
i) a glycidylester of the general formula I

I in which
$R_1$ and $R_4$ are independently $C_1$–$C_6$ alkyl or $C_6$–$C_{10}$ cycloalkyl groups, and $R_2$ and $R_3$ are independently H or $C_1$–$C_6$ alkyl or $C_6$–$C_{10}$ cycloalkyl groups, and
ii) a curing compound selected from the group of amino resins blocked or unblocked (cyclo)aliphatic isocyanates, alpha,alpha'-dibranched cyclic anhydrides, acid-functional polyesters containing only alpha,alpha'-dibranched acid and ester groups, (cyclo)aliphatic amines, (cyclo)aliphatic polyamino amides, blocked or unblocked Lewis acids, and tertiary amines.

Preferably $R_1$ and $R_2$ are methylgroups, $R_3$ is hydrogen, and $R_4$ is an iso-butylgroup.

The novel epoxy resin is a low viscous, slightly yellow colored oil. Coatings based on this epoxy resin proved to be more resistant towards acids than coatings based on the diglycidylester of α,α-branched diethylmalonic acid.

In order to improve the present resin it is preferably reacted with a dicarboxylic acid to form a hydroxyl rich polyester.

This is called an advancement or fusion reaction. The obtained linear polymer is then cured via the hydroxyl groups using a curing agent.

Therefore the invention preferably relates to a thermosetting resin composition comprising
i) an advanced resin product obtainable by reacting
a) a diglycidylester of the general formula I

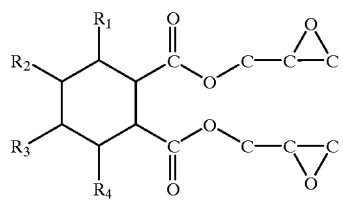

in which
$R_1$ and $R_4$ are the same or different $C_1$–$C_6$ alkyl or $C_6$–$C_{10}$ cycloalkyl groups, and $R_2$ and $R_3$ are the same or different and are H or $C_1$–$C_6$ alkyl or $C_6$–$C_{10}$ cycloalkyl groups, with
b) an alpha,alpha'-dibranched dicarboxylic acid of the general formula II

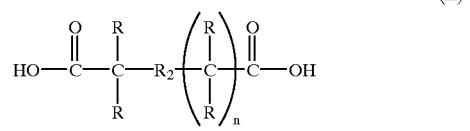

wherein n is 0 or 1,
wherein R is independently selected from the group consisting of straight and branched chain alkyl, cycloalkyl, arylalkyl and aryl, or both R's may form part of a substituted or unsubstituted cycloaliphatic ring system comprising 5, 6 or 8 carbon atoms, in which case n should be 0, and/or
c) an α,β-dibranched dicarboxylic acid

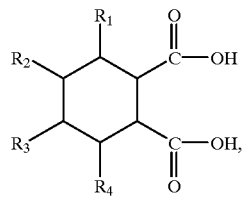

$R_1$, $R_2$, $R_3$ and $R_4$ being as broadly defined hereinbefore,
ii) a curing compound selected from the group consisting of amino resins blocked or unblocked (cyclo)aliphatic isocyanates, alpha,alpha'-dibranched cyclic anhydrides, acid-functional polyesters containing only alpha,alpha'-dibranched acid and ester groups, (cyclo)aliphatic amines, (cyclo)aliphatic polyamino amides, blocked or unblocked Lewis acids, and tertiary amines.

Advantageously $R_1$ and $R_2$ are methyl groups, $R_3$ is hydrogen, and $R_4$ is an iso-butylgroup.

It was surprisingly found that the combination of i) an advanced resin product of a diglycidylester of an alpha,beta-dibranched dicarboxylic acid with an alpha,alpha'-dibranched dicarboxylic acid and/or an alpha,beta-dibranched dicarboxylic acid and ii) a curing agent which cures via the hydroxyl and/or epoxy groups of the advanced resin product and which does not form any "weak" ester linkages (which are formed when curing with conventional anhydrides or polycarboxylic acids), has a significant positive effect on the weathering resistance of the resulting cured matrix.

Advancing of a) with b) and/or c) is generally carried out at a temperature of between 20° C. and 160° C. and the molar ratio of a) and b) and/or c) applied preferably lies within the range of from 0.5 to 2.0.

It is preferred to react a) and b) and/or c) in the absence of a solvent, however, if necessary a non-interfering solvent may be added to the reaction mixture, such as ketones, alcohols, ethers and aromatic hydrocarbons such as toluene and xylene.

In general no catalyst is needed in advancing a) with b) and/or c). However, if required any suitable catalyst may be added to the reaction mixture, for example tertiary phosphines and amines, quaternary phosphonium and ammonium salts and metal salts such as chromium salts.

The branched dicarboxylic acid c) may be the same or different branched dicarboxylic acid wherefrom compound a) is derived.

If desired mixtures of a) and/or b) and/or c) can be used.

Depending on the ratio of components a) and b) and/or c) applied in the advancing process the advanced resin product will generally be a mixture of essentially linear compounds carrying carboxy- or epoxy end groups. The number average molecular weight of the advanced product formed by reacting a) with b) and/or c) generally lies within the range of from 600 to 7000; this of course depends on the sort of starting compounds a) and b) and/or c) and their molar ratio in the reaction mixture. The advanced resin product may vary from oil type liquid to highly viscous or solid products.

Terminal epoxy—or carboxy groups of the advanced resin product may be converted into secondary hydroxyl groups. This can be achieved during the reaction of a) with b) and/or c) or after completion of the reaction of a) with b) and/or c). To that end the epoxy end groups can be reacted with a stoichiometric quantity of an alpha-branched monocarboxylic acid such as dimethylpropionic acid, hydroxypivalic acid or one of the commercially available tertiary monocarboxylic acids containing of from 5 to 10 carbon atoms known as VERSATIC acids (VERSATIC is a trade mark), likewise carboxy end groups can be reacted with a stoichiometric quantity of a monoglycidylester of an alpha-branched monocarboxylic acid such as for example one of the commercially available glycidylesters of the VERSATIC acids, known as CARDURA (CARDURA is a trade mark).

Compounds b) can be prepared by methods known in the art e.g. as described in U.S. Pat. No. 3,644,431.

As preferred compounds b) can be mentioned those wherein R is $C_1$ to $C_4$ alkyl.

Typical compounds b) are the diglycidylesters of dimethylmalonic acid, diethylmalonic acid (DEMA), dibenzylmalonic acid, tetrapropyladipic acid (TPAA), tetramethylenecyclohexyladipic acid, sulphodipivalic acid (SDPA), 1,1- dicarboxy-2-phenyl-4-methyl cyclohexane, 1,1-dicarboxy-2-ethyl-4-methyl cyclohexane, 2,2,6,6-tetramethyl-3-keto-4-oxapimelic acid and 1,4-dicarboxy-1,4-dimethyl cyclohexane.

Preferred compounds b) are the diglycidylesters of DEMA, TMAA, SDPA and TPAA.

Similarly, typical and preferred compounds c) are the dicarboxylic acids mentioned above in connection with the typical compounds a).

The advanced epoxy resin product can be used alone or in combination with other curable epoxy resin compounds in the thermosetting resin composition of the invention.

The thermosetting resin composition according to the invention comprises a curing compound which cures via the hydroxyl and/or epoxy groups of the advanced product, in such a way that ether, amine, urethane or alpha'-dibranched ester linkages are formed but unbranched ester linkages are avoided. Typical curing agents are melamine-formaldehyde resins such as hexamethoxymethylmelamine (HMMM), urea-formaldehyde resins, glycouril resins, alcohol-blocked isophorone diisocyanates, 3,3,4,4-tetramethylsuccinic anhydride, isophorondiamine, Versamid 100 (an aminoamide), dicyandiamide, boron-trifluoride-ethylamine complex, and N,N,N',N'-tetramethyl-1,6-diaminohexane. A particularly preferred curing compound is hexamethoxymethylmelamine (HMMM).

Depending on the choice of curing compound the cure can be effected in one or more cycles at temperatures of from 80° C. to 200° C., preferably of from 140 to 170° C. for a period of from 5 to 30 minutes.

Although cross-linking mainly takes place between the OH groups and the curing compound, the epoxy or carboxy end groups present in the advanced resin product may also participate in the cross-linking. It is furthermore possible to use accelerators in the curing reaction, suitable accelerators for amino type curing agents are e.g. acids such as phosphoric acid, para-toluene sulphonic acid (pTsa), Lewis acids and blocked Lewis acids such as $BF_3$-amine adducts; suitable accelerators for isocyanate type curing agents are e.g. tertiary amines, phosphines and metal salts such as dibutyl tindilaurate.

The thermosetting resin composition according to the invention may further at any stage before cure be mixed with usual modifiers such as extenders, fillers pigments, dyestuffs, organic solvents, flow control agents and agents for conferring thixotropy.

Suitably organic solvents useful for modifying the curable thermosetting composition according to the invention are e.g. toluene, xylene, n-propanol, butylacetate, acetone, methyl-ethyl ketone, diacetone-alcohol, ethylene glycol monomethyl ether and ethylene glycol monobutyl ether.

The thermosetting resin compositions of the invention can be used in solvent or water borne paints as well as in powder coating systems, which can be cured into insoluble and infusible weathering resistant coatings.

Due to the $\alpha,\beta$-dibranched ester structures the resin compositions according to the invention are especially suitable for the production of water borne paints of high hydrolytic stability.

Typical enduses of the composition according to the invention are seen in decorative paint systems e.g. for automotive topcoats.

The following examples are presented to illustrate certain specific embodiments of the present invention but are not to be considered limitative thereto.

EXAMPLE I

Chemicals used

Maleic anhydride was obtained from Merck or from Janssen Chimica and was used without further purification. (4E,6E)-2,6-Dimethyl-2,4,6-octatriene (allo-ocimene) was obtained from Aldrich and from the company Bush, Boake Allan Ltd. and was distilled before use. The allo-ocimene from Aldrich was 90% pure, and contained about 6% of the trans isomer, 2.5% of limonene, and about 1% of an allo-ocimene dimer.

Preparation of 5,6-dimethyl-3-isobutenyl-tetrahydrophthalic anhydride (1)

Maleic anhydride (39.88 g), 0.407 mol) and allo-ocimene (55.34 g, 0.407 mol) were charged in a 250 ml three necked round-bottom flask, connected with a reflux condenser. Immediately after addition of the maleic anhydride to the allo-ocimene, the mixture turned intense orange/yellow. The mixture was warmed carefully to 50° C. Then, as the maleic anhydride started to melt, a violent and exothermic Diels-Alder reaction took place. The temperature rose rapidly to 170–190° C. while the color of the mixture became less intense. After about 10 minutes the temperature started to drop. The mixture was kept at 100° C. for one hour. 93.71 g (0.401 mol=98.4%) of a yellow product was obtained that solidified on standing (melting point 78–82° C.). The product was washed with pentane in order to remove the yellow color to a great extent. The yield dropped during washing to about 65%. The anhydride was recrystallized from heptane to yield a white solid (melting point 83.5° C.–84° C.). Yield after recrystallization was 60%).

Preparation of 5,6-dimethyl-3-isobutylhexahydrophthalic anhydride (2)

A 250 ml autoclave was charged with a solution of 4,5-cyclohexene-5,6-dimethyl-3-isobutenyl-1,2-dicarboxylic anhydride (32.0 g, 136.7 mmol) in 210 ml ethylacetate. 0.2 g $PtO_2$ (Adams catalyst) was added. The solution was stirred using a magnetic stirrer. Hydrogenation was achieved in 2½ hours at 40–50° C. using 30 bars $H_2$. The catalyst was filtered off and the solution was concentrated in vacuo, to yield 32.12 gram (135.0 mmol, 98%) of 2,3-dimethyl-5-isobutylhexahydrophthalic anhydride.

Preparation of 5,6-dimethyl-3-isobutylhexahydrophthalic acid

The obtained anhydride (2) was transformed into a dicarboxylic acid. A 100 ml three necked round-bottom flask was charged with the anhydride (2.01 g; 8.45 mmol), water (50 ml) and KOH (1.18 g; 21.1 mmol). The mixture was refluxed for 90 minutes. After cooling to room temperature the mixture was extracted with diethylether (30 ml). The aqueous layer was acidified with a 1 N HCl solution to pH=1. The acid precipitates as a yellowish gummy material, which was dissolved in 50 ml of diethylether, washed with water (30 ml) and concentrated in vacuo, to yield 2.09 gram (97%).

Preparation of the diglycidylester of 2,3-dimethyl-5-isobutylhexahydrophthalic anhydride 2,3-Dimethyl-5-isobutylhexahydrophthalic anhydride (2) was transformed into the diglycidylester. To this end a 500 ml standard reactor was charged with the anhydride (48.42 g, 203.4 mmol), epichlorohydrine (188.2 g, 2.034 mol), isopropanol (110.0 g, 1.831 mol) and water (89.4 g, 4.96 mol). The mixture was stirred at 80° C., while 7.60 gram (95.0 mmol) of a 50 wt % solution of NaOH was added at once (about 20% of the total caustic needed). After stirring at 80° C. for one hour, the remainder of the caustic solution (30.48 g, 381 mmol) was added dropwise during 90 minutes. The mixture was stirred for another 15 minutes at 80° C., and then the brine was separated. The organic layer was washed with 75 ml of a 10 wt % $NaH_2PO_4$ solution and subsequently with demineralized water. After concentration in vacuo 46.97 g (97%) of a crude epoxy resin was obtained as a yellow low-viscous oil.

The crude resin had an epoxy group content (EGC) of 4600 mmol/kg and contained 18,000 ppm hydrolysable chlorine. The resin was given a so-called after dehydro chlorination treatment (ADHC) as a 30 wt % solution in MIBK. Thus, 46.97 g of the crude resin was dissolved in 160 ml MIBK. At 45° C., 3.81 g (47.6 mmol) of a 50 wt % NaOH solution was added at once. Stirring was continued for one hour, then the aqueous layer was diluted with 10 ml water and separated. The organic layer was washed with 60 ml of a 10 wt % $NaH_2PO_4$ solution and subsequently with 60 ml demineralized water. The yellow color of the crude resin weakened considerably during the ADHC treatment. The resin had an EGC 4810 mmol/kg (88.5% of theoretical) and a hydrolysable chlorine content of 2030 ppm. The total chlorine content of the resin was 2800 ppm.

Glycidation of related compounds

We have also glycidated two anhydride compounds related to compound (2), i.e. the unsaturated Diels-Alder adduct (1) and the aromatic anhydride (4). This latter anhydride was obtained by heating the neat Diels-Alder adduct in the presence of palladium in an inert atmosphere. We have found that a yield of 83% was obtained when the reaction was performed at 225° C. for 5 hours. The product (4) was a white solid that can be recrystallized from methanol (mp 92° C.).

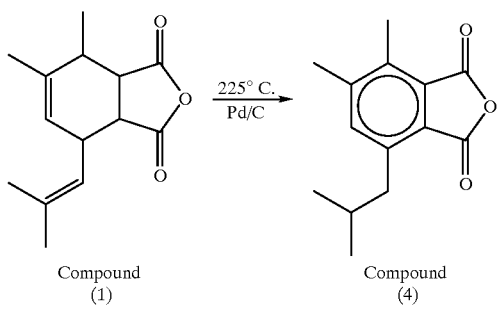

The conditions for the glycidation reactions were the same as for the glycidation of the saturated anhydride (2). Also, the conditions of the applied ADHC treatment were identical.

In Table I, some results of these glycidation reactions are summarized. For comparison, also data about the glycidation of hexahydrophthalic anhydride (HHPA) are included in this table. The yield of the glycidation reaction of compound (2) is remarkable high, especially in comparison with that of HHPA. Apparently, β-substitution works, and the β-branching in compound (2) is indeed responsible for an adequate protection against hydrolysis.

It appears that the glycidation of the unsaturated anhydrides (1) and (4) and that of HHPA yields epoxy resins with a higher hydrolysable chlorine content and a higher total chlorine content than glycidation of the saturated anhydride (2). The diglycidylesters of compound (1) and (4) have not been used to make coatings, but have been prepared for comparison reasons.

TABLE I

Comparison of some resin characteristics of glycidated anhydride

| | anhydride (2) | anhydride (1) | anhydride (4) | HHPA |
|---|---|---|---|---|
| yield | 97% | 84% | 81% | 86% |
| EGC (mmol/kg) | 4810 | 4430 | 4270 | 6410 |
| (5 of theoretical) | 88.5% | 81% | 77% | 91% |
| Hydrolysable chlorine before ADHC | 18,000 | 32,000 | 48,000 | 40,000 |
| Hydrolysable chlorine after ADHC | 2030 | 4300 | 4050 | 3800 |
| Yield ADHC | 87% | 84% | 80% | 82% |
| Total chlorine after ADHC | 2800 | 5700 | 5100 | 4600 |

EXAMPLE II

We have prepared two different types of advanced resins. One is made from the diglycidylester (5) as depicted in page 5 advanced with its own precursor acid (binder resin A), the other one is made from the diglycidylester (5), advanced with butyl ethylmalonic acid (binder resin B). The advancement reaction was performed without a solvent or catalyst at 160° C. (for binder resin A) or 120° C. (for binder resin B). During the advancement reaction, the epoxy group content (EGC) and the acid value (AV) were being monitored. The reaction was stopped when no acid groups were left, and the theoretical EGC was achieved. Fortunately, the EGC and the AV decreased at exactly the same rate. This indicated that no side reactions occurred.

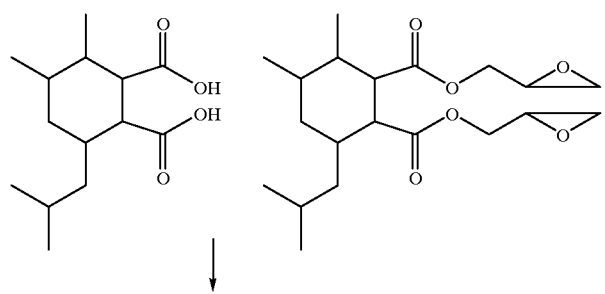

-continued

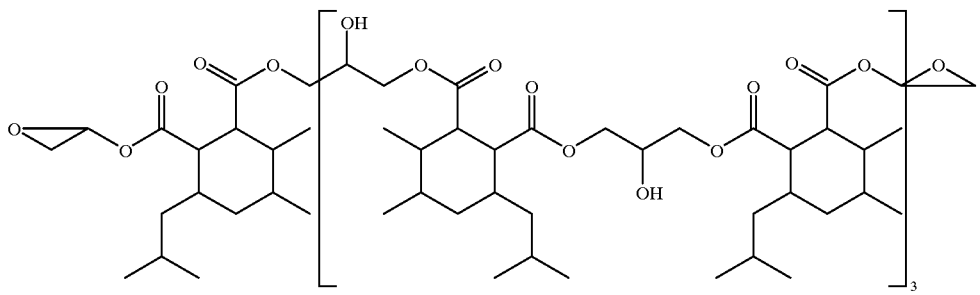

The advanced resin was mixed with melamine resin, applied on steel panels by a bar-coater, and cured in an oven at 160° C.

The acid resistance of the coatings was tested by applying drops of different acids (HCl, $H_2SO_4$, and $H_3PO_4$:0.16 N) on the coatings, and putting them horizontally in an oven at 50° C. for 30 min. Afterwards, the coatings were inspected visually. Clearly, the acid resistance of the coatings based on binder resin A and B is far better than that of coatings based on the diglycidylester of diethylmalonic acid (DGEDEMA). Other properties of the new epoxy based coating are comparable with the properties as obtained with DGEDEMA.

We claim:

1. A glycidylester of the general formula I

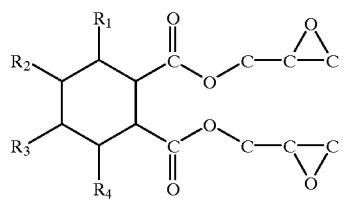

in which $R_1$ and $R_2$ are methyl groups, $R_3$ is hydrogen, and $R_4$ is an iso-butyl group.

2. The glycidylester of claim 1 wherein the glycidylester has been prepared by:

reacting allo-ocimene and maleic anhydride to form an addition product.

3. A glycidylester of the general formula I

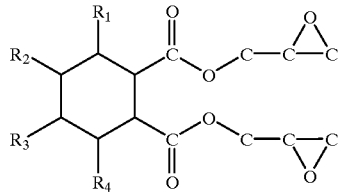

in which $R_1$ and $R_2$ are methyl groups, $R_3$ is hydrogen, and $R_4$ is an iso-butyl group;

wherein the glycidylester has been prepared by reacting a diene and maleic anhydride to form a Diels-Alder addition product, hydrogenating and hydrating the addition product to an α,β-substituted di-carboxylic acid; and then glycidating the dicarboxylic acid.

* * * * *